US00PP07765P

United States Patent [19]

Matoba

[11] Patent Number: Plant 7,765

[45] Date of Patent: Jan. 14, 1992

[54] 'RED NUGGET' PLUM TREE

[76] Inventor: Frank T. Matoba, 4890 S. DeWolf Ave., Del Rey, Calif. 93616

[21] Appl. No.: 534,659

[22] Filed: Jun. 4, 1990

[51] Int. Cl.[5] ..... A01H 5/00

[52] U.S. Cl. ..... Plt./38

[58] Field of Search ..... Plt. 38, 38.1

[56] References Cited

U.S. PATENT DOCUMENTS

Plt. 3,811 11/1975 Zaiger ..... Plt. 38

*Primary Examiner*—Howard J. Locker

*Attorney, Agent, or Firm*—Worrel & Worrel

[57] ABSTRACT

A new and distinct variety of plum tree derived as an open pollinated hybrid of the 'Red Beaut' plum tree (U.S. Plant Pat. No. 2,539) producing a medium red, semi-clingstone fruit having noteworthy shipping and handling characteristics for an early plum and which are mature for harvesting and shipment approximately May 10 to May 15 in the San Joaquin Valley of central California, or approximately ten days before the fruit of the 'Red Beaut' plum tree.

1 Drawing Sheet

BACKGROUND OF THE NEW VARIETY

The present invention relates to a new and distinct variety of plum tree which will hereinafter be denominated varietally as 'Red Nugget' and more particularly to a plum tree which produces medium red fruit which are very early ripening, maturing for harvest approximately May 10 to May 15 in the San Joaquin Valley of central California, or approximately ten days before the fruit of the 'Red Beaut' plum tree.

The development of new varieties of fruit trees and the selection of those new varieties having promising commercial potential requires the assiduous consideration of a host of characteristics. The principal characteristics of the fruit, such as ripening date, size, color, flavor, handling characteristics and resistance to disease, vary substantially from one variety to another so that the selection requires a balancing as to importance of these characteristics in making the selection. Thus, for a variety which produces an early or late ripening fruit, characteristics of size and coloration may not be as important as in the case of a variety producing fruit which ripens during more typical portions of the harvesting season. Stated in other terms, a premium has always been placed on varieties producing fruit which ripen early or late in the harvest season. Where the fruit of such varieties also possesses superior attributes in other characteristics as well, the commercial potential of those varieties is accordingly very promising.

ORIGIN AND ASEXUAL REPRODUCTION OF THE NEW VARIETY

The present variety of plum tree hereof was discovered by the inventor in his parents' orchard which is located at 4890 South DeWolf, Del Rey, Calif. 93616. The new variety is an open pollinated seedling of the 'Red Beaut' plum tree discovered in 1985 by the inventor from approximately five thousand test seedlings.

The new variety of plum tree was asexually reproduced by budding and whip grafting at the inventor's direction in 1986 on the same property and those trees bore some fruit in 1987 and 1988 at which time the inventor confirmed that the same distinctive characteristics were reproduced in the progeny as shown in the parent seedling. Since that time many more trees of the new variety have been asexually reproduced and planted in other test locations to confirm that the same distinctive characteristics were found in the trees of the new variety grown under other soil and farming conditions.

SUMMARY OF THE NEW VARIETY

The 'Red Nugget' plum tree is characterized as to novelty by producing fruit of medium red coloration which are very early ripening being ready for harvest approximately May 10 to May 15 in the San Joaquin Valley of central California, or about ten days before the 'Red Beaut' plum (U.S. Plant Pat. No. 2,539) tree from which it was derived as an open pollinated hybrid. It is possible, although it is not known, that the pollinator variety was the 'Santa Rosa' plum tree. The fruit has noteworthy shipping and handling characteristics for an early plum with a pleasing flavor and good aroma.

BRIEF DESCRIPTION OF THE DRAWING

The drawing is a photograph of the new variety showing representative fruit thereof, one being disposed in side elevation, a second in side elevation with the stem visible, a third sectioned to show the flesh thereof, a fourth in bottom plan view showing the apex end and a fifth in top plan view showing the stem cavity; a stone of the new variety; and representative foliage thereof.

DETAILED DESCRIPTION

Referring more specifically to the pomological details of this new and distinct variety of plum tree, the following has been observed under the ecological conditions prevailing at the orchard of origin which is located in the San Joaquin Valley of central California. All major color code designations are by reference to the Dictionary of Color, by Maerz and Paul, Second Edition, 1950. Common color names are also employed occasionally where believed to be assistance.

TREE

Generally:

*Size.*—Medium.

*Figure.*—Upright.

*Productivity.*—Productive.

*Regularity of bearing.*—Regular.

Trunk:

*Size.*—Stocky.
*Surface texture.*—Rough.
Branches:
*Size.*—Medium.
*Surface texture.*—Rough with zig-zag lighter colored lines.
*Color.*—Multi-base color Page 71, Plate 24, E-C; Zig-zag Lines — Page 47, Plate 12, G-7.
*Lenticels.*—Numbers — Numerous. Size — 0.02 mm (0.00079 inch) to 0.1 mm (0.0039 inch)×0.02 mm (0.00079 inch) to 8 mm (0.315 inch).

LEAVES

Size:
*Generally.*—Medium.
*Average length.*—77 mm (3.031 inches) to 81 mm (3.189 inches).
*Average width.*—33 mm (1.299 inches) to 36 mm (1.417 inches).
Form: Oblanceolate.
Color:
*Upwardly disposed surface.*—Page 69, Plate 23, L-12.
*Downwardly disposed surface.*—Page 69, Plate 23, L-1.
Marginal form: Double serrate.
Glandular characteristics of leaves: no glands present.
Petiole:
*Length.*—14 mm (0.55 inch) to 16 mm (0.630 inch).
*Thickness.*—1 mm (0.039 inch).
Stem glands:
*Type.*—Globose.
*Arrangement.*—Irregular.
*Color.*—Reddish.
Stipules: None.

FLOWERS

Flower buds:
*Size.*—Small 4 mm. (0.157 inch).
*Surface texture.*—Glabrous.
Flowers:
*Generally.*—Short, conic and plump.
*Date of bloom.*—About Feb. 23, 1991. Approximately simultaneously with the 'Ambra' plum tree on Feb. 23, 1991 and the 'Santa Rosa' plum tree on Feb. 23, 1991 to Feb. 25, 1991.
*Size.*—Generally — small, 16 mm (0.630 inch) to 20 mm (0.787 inch) when open.
*Petals.*—Color — white.
*Stamens.*—Twenty-nine to thirty-one.
*Pistil.*—One.

FRUIT

Maturity when described: Ripe for commercial harvesting and shipment approximately May 10 to May 15, or approximately ten days before the fruit of the 'Red Beaut' plum tree, in the San Joaquin Valley of central California.
Size:
*Generally.*—Small and uniform.
*Average diameter.*—44 mm (1.732 inches) to 46 mm (1.811 inches).
*Average diameter transverse in the suture plane.*—42 mm (1.654 inches) to 44 mm (1.732 inches).
*Average diameter transverse and at right angles to the suture plane.*—42 mm (1.654 inches) to 44 mm (1.732 inch).
*Form.*—Uniformity — uniform. Symmetry — symmetrical.
*Suture.*—Generally — distinct — slightly depressed. Length — 62 mm (2.440 inches) to 65 mm (2.559 inches). Position — has slight depression beyond pistil point.
*Ventral surface.*—Generally — smooth.
*Stem cavity — generally.*—acute angle.
Stem cavity.—8 mm (0.315 inch)×17 mm (0.669 inch) ×7 mm (0.276 inch) deep.
*Base.*—Slightly rounded.
*Apex.*—Slightly prolonged.
*Pistil point.*—Some depressed and some pointed.
*Stem.*—Length — 11 mm (0.433 inch). Caliper — 2 mm (0.079 inch).
Skin:
*Thickness.*—Medium.
*Texture.*—Medium.
*Tendency to crack.*—None.
*Color.*—Page 37, Plate 7, J-6.
*Pubescence.*—None.
Flesh:
*Flesh color.*—Page 45, Plate 11, L-11.
*Surface of pit cavity.*—Smooth, same color as flesh.
*Color of pit well.*—Same color as flesh.
*Amygdalin.*—Scant.
*Juice production.*—Juicy.
*Flavor.*—Pleasing.
*Aroma.*—Good.
*Texture.*—Smooth, melting.
*Fibers.*—Texture — Fine.
*Ripening.*—Even.
*Eating quality.*—Good.
Stone:
*Attachment.*—Semi-cling.
*Fibers.*—Length — Short.
*Size.*—Length — 18 mm (0.709 inch). Width — 16 mm (0.630 inch) in suture plane. Thickness — 8 mm (0.315 inch).
*Form.*—Generally — oval.
*Apex.*—Shape — pointed.
*Color.*—Page 47, Plate 12, H-7.
*Base.*—Shape — Flat.
*Sides.*—Oval, pointed at apex.
*Ridges.*—Few at base, some at apex.
*Tendency to split.*—None.
Use: Fresh market.
Keeping quality: Good for early plum.
Shipping and handling qualities: Good for early plum.

Although the new variety of plum tree possesses the described characteristics noted above as a result of the growing conditions prevailing near Del Rey in the San Joaquin Valley of central California, it is to be understood that variations of the usual magnitude and characteristics incident to changes in geographical location, growing conditions, rootstock, fertilization, pruning and pest control are to be expected.

Having thus described and illustrated my new variety of plum tree, what I claim as new and desire to be secured by Plant Letters Patent is:

1. A new and distinct variety of plum tree substantially as illustrated and described and which produces small and uniform, medium red semi-clingstone fruit having noteworthy shipping and handling characteristics for an early plum and which are mature for harvesting and shipment approximately May 10 to May 15 in the San Joaquin Valley of central California, or approximately ten days before the fruit of the 'Red Beaut' plum tree.

* * * * *

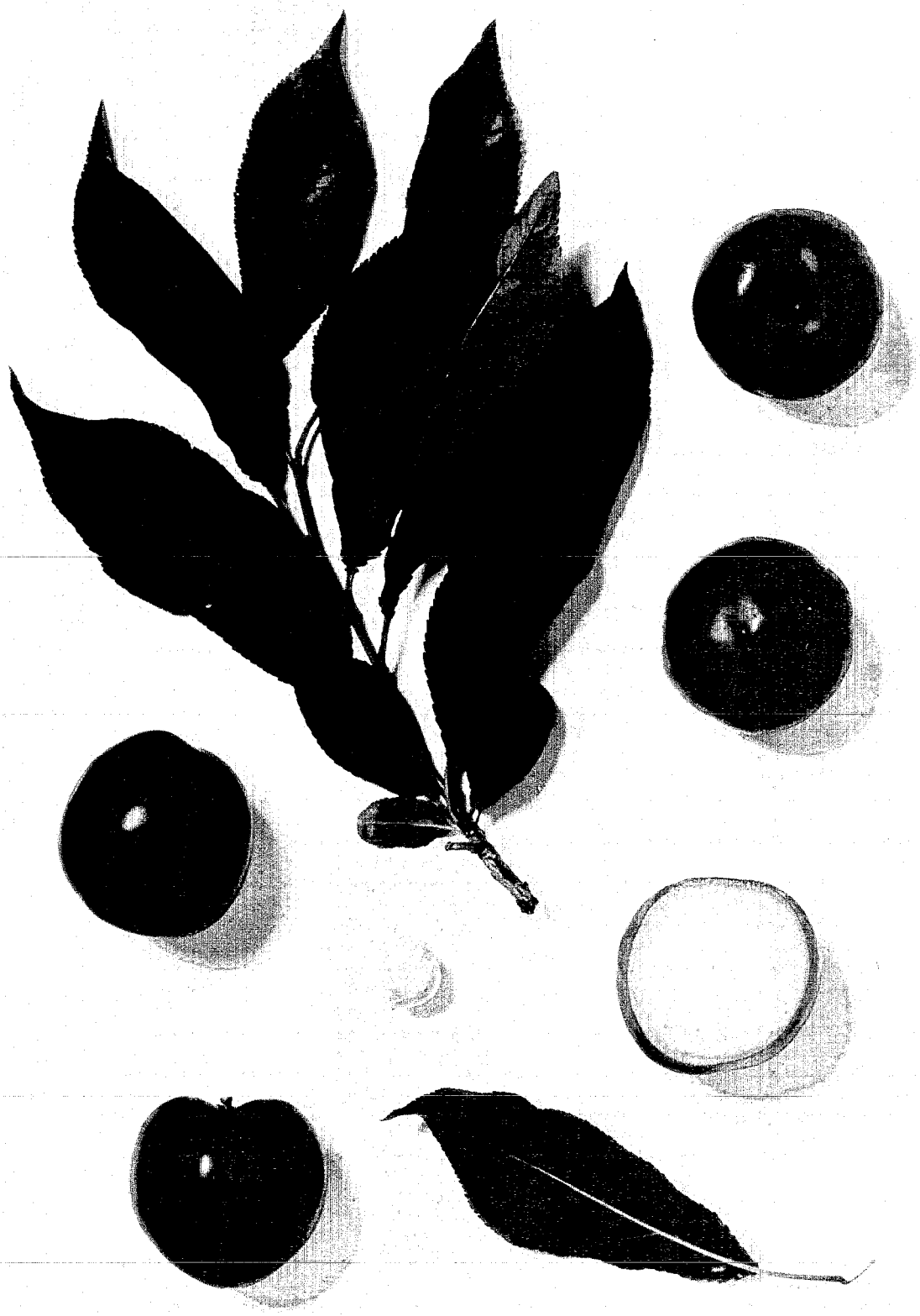

UNITED STATES PATENT AND TRADEMARK OFFICE

CERTIFICATE OF CORRECTION

PATENT NO. : Plant 7,765

DATED : January 14, 1992

INVENTOR(S) : Frank T. Matoba

It is certified that error appears in the above-identified patent and that said Letters Patent is hereby corrected as shown below:

Column 2, Line 38, Between "be" and "assistance,"

insert---of

Signed and Sealed this

Sixth Day of April, 1993

*Attest:*

STEPHEN G. KUNIN

*Attesting Officer*

*Acting Commissioner of Patents and Trademarks*